United States Patent [19]

Weststrate et al.

[11] Patent Number: 4,460,565

[45] Date of Patent: Jul. 17, 1984

[54] ANTICARIOGENIC REMINERALIZING DENTIFRICE

[75] Inventors: Jan Weststrate; Ede M. Staal, both of Amersfoort, Netherlands

[73] Assignee: Intradal N.V., Amersfoort, Netherlands

[21] Appl. No.: 394,725

[22] Filed: Jul. 2, 1982

[30] Foreign Application Priority Data

Jul. 3, 1981 [NL] Netherlands .......................... 8103209

[51] Int. Cl.$^3$ .......................... A61K 7/16; A61K 7/18
[52] U.S. Cl. ........................ 424/52; 424/49; 424/57
[58] Field of Search ............................. 424/49, 52, 57

[56] References Cited

U.S. PATENT DOCUMENTS

| | | | |
|---|---|---|---|
| 2,191,199 | 2/1940 | Hall | 424/57 |
| 2,216,816 | 10/1940 | Kuever | 424/57 |
| 3,699,220 | 10/1972 | Weststrate et al. | 424/57 |
| 3,929,493 | 12/1975 | Lee et al. | 424/357 |
| 3,966,863 | 6/1976 | Forward et al. | 424/52 |
| 4,080,440 | 3/1978 | Diguilio et al. | 424/52 |
| 4,083,955 | 4/1978 | Grabenstetter et al. | 424/52 |
| 4,108,980 | 8/1978 | Duff | 424/57 |
| 4,141,969 | 2/1979 | Mitchell | 424/52 |
| 4,152,419 | 5/1979 | Pensak | 424/57 |
| 4,159,280 | 6/1979 | Wason | 424/52 |
| 4,177,258 | 12/1979 | Gaffar et al. | 424/57 |
| 4,193,988 | 3/1980 | Forward et al. | 424/57 |
| 4,198,394 | 4/1980 | Faunce | 424/57 |
| 4,244,931 | 1/1981 | Jarvis et al. | 424/57 |
| 4,314,990 | 2/1982 | Denny et al. | 424/57 |
| 4,340,583 | 7/1982 | Wason | 424/57 |
| 4,349,533 | 9/1982 | Dent et al. | 424/52 |
| 4,357,317 | 11/1982 | Weyn et al. | 424/57 |
| 4,358,437 | 11/1982 | Duke | 424/52 |

*Primary Examiner*—Shep K. Rose
*Attorney, Agent, or Firm*—Cushman, Darby & Cushman

[57] ABSTRACT

A dentifrice containing two or more fluorine compounds, at least one soluble salt producing phosphate ions, and at least one substance providing calcium ions, and as a result thereof having good remineralization properties. Preferred compositions contain as the fluorine compounds a fluoride and a monofluorophosphate, as phosphate compounds a cyclic metaphosphate and a linear phosphate, and as calcium compound a calcium salt of an organic acid.

19 Claims, No Drawings

ANTICARIOGENIC REMINERALIZING DENTIFRICE

This invention relates to dentifrices having an increased anticariogenic effect, and also capable of fully or partially restoring carious tooth parts.

As used in this application, the term dentifrices means products which remain in the mouth for a relatively short period of time, in which they are intimately contacted with substantially all surfaces of the teeth, and are then removed.

Examples of such products are toothpastes, prophylactic pastes, tooth polishes, mouth waters, application liquids and gels, specific chewing gums, etc.

It has long since been known that the addition of fluorine compounds to such dentifrices can significantly reduce caries progression.

In the incorporation of the fluorine compound, however, the problem was encountered that these materials turned out to be incompatible, or poorly compatible with a number of much-used basic raw materials.

Especially in the application in tooth paste, many problems were encountered. In order to provide good compatibility between the fluorine compound, on the one hand, and the other ingredients, on the other, new fluorine compounds and new raw materials (in particular polishing agents) were developed.

Fundamental research into the compatibility of some fluorine compounds with the most usual toothpaste ingredients was conducted by Ericsson in 1962. His work was concerned in particular with a fluorine compound that was rather new at the time: the sodium monofluorophosphate.

In this substance, the fluorine ion is complexly bound and, as a result, less reactive relative to the other components.

As the sodium monofluorophosphate has an extremely good anticariogenic activity, this fluorine compound is now most frequently used in dentifrices. Other fluorine compounds, in particular NaF and $SnF_2$, have also proved to be effective in clinical trials, but these fluorine compounds could not be used until after special raw materials had been developed that were capable of being combined with these fluorine compounds. Among these are, in particular, the polishing agents, such as special polishing agents of synthetic resin material for dentifrices containing NaF, and special polymeric and pyrophosphates for dentifrices containing $SnF_2$.

In addition to these three most frequently used fluorine compounds, many other fluorine compounds are known and suitable for use. Among these may be mentioned fluorides, such as aluminum fluoride, cesium fluoride, cupric fluoride, ferric fluoride, magnesium fluoride; fluorophosphates, such as monofluorophosphates, difluorophosphates and polyfluorophosphates, e.g. calcium monofluorophosphate, sodium difluorophosphate, vanadium monofluorophosphate, and lithium mononfluoropolyphosphate.

Other suitable inorganic fluorine compounds are hexafluorosilicates, silico fluoric acid and zirconium germanium fluorides, while organic fluorine compounds, such as aminehydrofluorides, imidazolehydrofluorides, quaternary ammonium fluorides, aminofluorophosphates, hydrofluorides of amino acid derivatives and fluoridated biguanide compounds are also suitable.

Scientific investigation into the effect of the fluorine compounds has shown that various reaction mechanisms play a role. The classical explanation for the cariostatic effect of fluorine compounds is that hydroxyapatite reacts with the fluoride ion and is thereby converted into fluoridated hydroxyapatite.

This material is less soluble in acid medium than hydroxyapatite. As a consequence, after a fluorine application, the tooth is better protected from the acid surges which initiate the caries process.

In addition to this mechanism, others have been proposed, such as blockage of screw dislocations in the apatite crystal, kink-site-poisoning, etc. An important theory, which has been given further scientific basis in the last few years, starts from the influence of the fluoride ion on the remineralization process.

Remineralization of dental enamel means the phenomenon that hydroxyapatite may be formed from substances occurring naturally in saliva, in particular in places where the hydroxyapatite has disappeared in a preceding phase.

In the mouth, there is a natural equilibrium between hydroxyapatite being dissolved from the teeth, on the one hand, and hydroxyapatite being formed on or in the teeth from the saliva, on the other. This equilibrium is shifting continuously. Among other factors, it is determined by diet and physical condition. If the equilibrium is such that hydroxyapatite is dissolved, this is referred to as demineralization, and a carious condition arises. If the equilibrium is such that hydroxyapatite is being formed, this is referred to as remineralization. By remineralization, initial tooth decay can be restored by natural means.

It has been found that fluorine compounds, even in low concentrations, promote remineralization. Possibly, this mechanism gives even better protection against tooth decay than the decrease in acid solubility owing to fluoroapatite formation, referred to hereinbefore.

The degree in which the various fluorine compounds promote the remineralization process differs greatly. Also, the effectiveness with which fluoride is incorporated varies depending on the various fluorine compounds used in fluoride applications.

It is desirable that an optimum effect is obtained from the known protection mechanisms, and this can be achieved, inter alia, by using a combination of two or more fluorine compounds. Our investigations have shown that the combination of a fluoride, e.g. sodium fluoride, together with a monofluorophosphate, e.g. sodium monofluorophosphate gives the best results.

The ratio of sodium fluoride:sodium monofluorophosphate of 3:1 (as $F^-$) is particularly preferred.

For determining the optimum fluoride ratio, use was made, inter alia, of a RES (Reduction Enamel Solubility). In this test, a thoroughly cleaned bovine tooth is treated in a toothpaste suspension (1:3 dilution) at a temperature of 37° C. for 24 hours. After rinsing and cleaning the tooth it is placed in an acetate buffer (pH 5.0) for 24 hours, whereafter the amount of calcium and phosphate dissolved is measured in $\mu$moles per $cm^2$ tooth enamel. A tooth treated with water is used by way of control. For a paste containing 1500 ppm fluorine (calculated as F), the following reductions were found:

| MEP in ppm F | 0 | 1500 | 1125 | 750 | 375 | 0 | control |
|---|---|---|---|---|---|---|---|
| NaF in ppm F | 0 | 0 | 375 | 750 | 1125 | 1500 | A. Dist. |
| μMol Ca/cm$^2$ | 106.6 | 91.0 | 72.1 | 64.3 | 53.5 | 75.5 | 111.0 |
| | | | | | | | (101.6–118.7) |
| μMol PO$_4$/cm$^2$ | 58.9 | 52.7 | 40.3 | 36.0 | 30.0 | 43.4 | 62.0 |
| | | | | | | | (53.8–73.3) |
| Av. % reduction rel. to control | 4.5 | 16.5 | 35 | 42 | 52 | 31 | — |

It is known that cyclic phosphates and in particular cyclic trimetaphosphates synergistically increase the cariostatic effect of monofluorophosphates. In order to obtain an optimum effect of the monofluorophosphate in the dentifrices, it is therefore desirable to add a minor quantity of cyclic phosphate. Sodium trimetaphosphate is preferred for this purpose, which in combination with sodium monofluorophosphate in a toothpaste was investigated in clinical trials, in which very high caries reductions were found. The usual concentrations ranged from 0.1 to 5%, and preferably between 0.25 and 2% of cyclic phosphate is used.

The total quantity of fluorine compounds that can be added to the dentifrices according to the invention depends in particular on the product in which they are used. A criterion for the maximum concentration of fluoride that can be used is the average quantity of product used per treatment, and also the frequency of use. The fluoride concentration should be selected to ensure that the toxic dose is not exceeded.

In toothpastes the total quantity of fluorine compounds is often that corresponding to 1000 to 1500 ppm F$^-$. In prophylactic pastes, this concentration is approx. 5 times higher, while application liquids and gels often contain 10,000 to 15,000 ppm F$^-$.

In fluoridated mouth washes for daily use, the total quantity of fluoride will be lower than in toothpaste. A suitable concentration in such liquids is 250 to 500 ppm F$^-$.

As far as can now be ascertained, the concentrations of fluoride being administered appear to be slightly too high for optimum remineralization. It is of importance, however, that such a quantity of fluoride is offered that a buffer stock is formed on the tooth—often in the form of calcium fluoride—which is capable of gradually giving up the fluorine to the saliva, owing to which the required, rather low fluoride concentration is present in the saliva for a longer period of time for optimum remineralization.

In addition to fluoride ions, it is of essential importance for dentifrices having a remineralizing effect to be capable of releasing both calcium ions and phosphate ions.

In the compositions according to the invention, two kinds of phosphates are used. In the first place, cyclic phosphates are present, which synergistically augment the action of the fluorine compound, and furthermore linear phosphates have been added for augmenting the remineralization process.

Suitable linear phosphates are phosphoric acid, sodium orthophosphate, sodium tripolyphosphate, sodium tetrapolyphosphate, sodium pyrophosphate, the linear sodium hexametaphosphate, etc.

Phosphates having a solubility in water >5% are particular suitable.

The linear phosphates are often, but not necessarily, used in a concentration lower than 5%. Preferably they are used in a stoichiometrical ratio to calcium as occurring in hydroxyapatite, i.e., 1.66 Ca:1 P.

The calcium ions are also essential for the remineralization process, even more so than the phosphate ions, because in the demineralization process, the calcium is the first to be dissolved from the hydroxyapatite. Indeed, demineralized tooth enamel, and also slightly carious enamel often has, relative to a decreased phosphate content, a much more greatly decreased content of calcium ions.

The administration of calcium ions in an effective form by means of dentifrices is not a simple matter. Calcium ions are rather reactive with the conventional ingredients for these products, and can lose their effectiveness virtually entirely by being chemically combined with these ingredients.

Thus calcium cannot just be added to dentifrices in the presence of phosphate ions, because the two will react with each other to form the calcium phosphate, which is hardly effective. By the same token, calcium ions cannot just be combined with fluoride ions, because of the precipitation of calcium fluoride, which is virtually ineffective. The problem of adding calcium ions in an effective form to dentifrices becomes still greater if sodium trimetaphosphate is present, because that compound is a very good calcium binder.

Accordingly, an excess of a calcium containing compound is not very possible, because the fluoride and the phosphate are then inactivated, but a low concentration of a calcium donor is also problematic, because in that case all of the calcium will be captured by the trimetaphosphate. Other ingredients are also capable of deactivating the calcium, but the above have been mentioned because of their adverse effect being dual. The calcium renders the cariostatic phosphate and fluoride ions inactive, and conversely these materials render the remineralizing calcium ions ineffective.

Surprisingly it has now been found that specific calcium complexes are capable of retaining the calcium in an active form in dentifrices without thereby deactivating other active materials.

It is an object of the present invention to provide dentifrices having optimum remineralization properties and containing calcium ions as well as phosphate ions and fluorine compounds in active form.

It has been found that calcium salts of organic acids, such as the calcium salts of citric acid, adipic acid, and tartaric acid satisfy the requirements made. Other suitable calcium donors have been found to be calcium-enriched minerals, such as calcium zeolite and calcium apofyllite. The calcium compounds are preferably used in a proportion of 0.05–5% by weight.

It has further been found that the pH of the dentifrices affects the remineralization process. Optimum exchange is possible in weakly acidic medium. Best results have been obtained at a pH of 6 to 7.

The effectiveness of the various dentifrices was assayed by means of critical-angle measurements on the tooth surface. By this method, the degree of surface remineralization is numerically expressed.

In the measurement, the critical angle is determined of a drop of water applied to a thoroughly cleaned piece of tooth enamel that has been ground to uniform smoothness. The first measurement is made before the test. A second measurement is made after the tooth has been demineralized with a 0.1M lactic acid/hydroxyl ethyl cellulose solution for 10 minutes. This demineralization decreases the critical angle by an average of 30° to 35°. Subsequently, the tooth is contacted for 30 minutes with a 30% suspension of toothpaste, or a solution of one of the other dentifrices, whereafter the critical angle is again measured.

In order to determine the residual effect after the treatment, the tooth is subsequently laid in an artificial saliva solution, and the progress of surface remineralization is determined at regular intervals by means of critical-angle measurements.

Starting from a paste as specified in the following Example 1, the following pastes were composed:
A. formulation according to Example 1, but without the active components.
B. Paste A plus sodium monofluorophosphate.
C. Paste A with sodium monofluorophosphate and sodium fluoride.
D. Paste C plus sodium phosphate and phosphoric acid.
E. Paste C with sodium trimethaphosphate.
F. Toothpaste according C with sodium phosphate/phosphoric acid and calcium citrate.
G. Toothpaste according C with sodium trimetaphosphate and calcium citrate.
H. Toothpaste according to C with phosphate/phosphoric acid and sodium trimetaphosphate and calcium citrate.

Results

1. Change of critical angle after 30 minutes' treatment with the toothpaste being tested.
2. Change of critical angle after 1 hour's storage in an artificial saliva solution.
3. Change in critical angle measured from demineralization up to, and including, treatment with artifical saliva.

|    | 1   | 2   | 3   |
|----|-----|-----|-----|
| A. | 0   | +8  | +8  |
| B. | +3  | +7  | +10 |
| C. | +5  | +6  | +11 |
| D. | +4  | +8  | +12 |
| E. | −16 | +28 | +12 |
| F. | +5  | +14 | +19 |
| G. | +8  | +12 | +20 |
| H. | +18 | +15 | +33 |

In column 3 the total effect is indicated. Compositions F, G and H according to the invention prove to give superior results.

EXAMPLES

| 1. Toothpaste | |
|---|---|
| Aluminum oxide | 35.0 |
| Silicon oxide | 2.0 |
| Glycerol | 20.0 |
| C.M.C. | 1.5 |
| Sodium laurylsulphate | 2.0 |
| Peppermint oil | 1.0 |
| Sodiumsaccharinate | 0.2 |
| Sodium fluoride | 0.22 |
| Sodium monofluorophosphate | 0.36 |
| Primary sodium phosphate | 0.40 |
| Phosphoric acid | 0.30 |
| Sodium trimetaphosphate | 0.25 |
| Calcium citrate | 0.6 |
| Na—methyl p-hydroxybenzoate | 0.10 |
| Water | ad 100 |
| 2. Toothpaste | |
| Calcium phosphate | 30.0 |
| Silicon oxide | 2.0 |
| Glycerol | 15.0 |
| Sorbitol | 10.0 |
| C.M.C. | 1.5 |
| Sodium laurylsulphate | 2.0 |
| Peppermint oil | 1.0 |
| Sodium saccharinate | 0.2 |
| Sodium fluoride | 0.22 |
| Sodium MFP | 1.0 |
| Primary sodium phosphate | 0.5 |
| Sodium TMP | 0.5 |
| Calcium tartrate | 0.2 |
| Citric acid | 0.1 |
| Sodium-methyl-p-hydroxybenzoate | 0.1 |
| Cryolite | 2.0 |
| Water | ad 100 |
| 3. Gel paste | |
| Silicon oxide | 20.0 |
| Glycerol | 50.0 |
| C.M.C. | 0.5 |
| Sodium lauryl sulphate | 1.5 |
| Peppermint oil | 1.0 |
| Sodium saccharinate | 0.1 |
| Sodium fluoride | 0.22 |
| Sodium MFP | 0.36 |
| Primary sodium phosphate | 0.5 |
| Sodium TMP | 0.25 |
| Calcium citrate | 0.3 |
| Citric acid | 0.2 |
| Sodium-methyl-p-hydroxybenzoate | 0.1 |
| Calcium zeolite | 0.5 |
| Water | ad 100 |
| 4. Fluoridated mouth wash (for weekly use) | |
| Sodium fluoride | 0.30 |
| Sodium MFP | 0.48 |
| Sodium phosphate | 0.4 |
| Phosphoric acid | 0.1 |
| Sodium TMP | 0.25 |
| Calcium citrate | 0.2 |
| Peppermint oil | 0.25 |
| Solubilizer | 0.75 |
| Sodium-methyl-p-hydroxybenzoate | 0.1 |
| Water | ad 100 |
| 5. Mouth wash (daily wash) | |
| Sodium fluoride | 0.08 |
| Sodium MFP | 0.12 |
| Sodium phosphate | 0.4 |
| Calcium citrate | 0.05 |
| Citric acid | 1.0 |
| Peppermint oil | 0.15 |
| Solubilizer | 0.45 |
| Ethyl alcohol | 30.0 |
| Sodium-methyl-p-hydroxybenzoate | 0.1 |
| Water | ad 100 |
| 6. Fluoride jelly | |
| Hydroxyethyl cellulose | 2.00 |
| Sodium fluoride | 0.66 |
| Sodium MFP | 0.80 |
| Sodium phosphate | 1.00 |
| Sodium TMP | 0.25 |
| Citric acid | 2.50 |
| Calcium citrate | 0.20 |
| Peppermint oil | 0.1 |
| Solubilizer | 0.4 |
| Water | ad 100 |

We claim:
1. A dentifrice having anticariogenic and remineralizing properties, comprising:

(a) a fluoride selected from the group consisting of alkali metal fluorides, alkaline earth metal fluorides, and ammonium fluoride;
(b) an alkali metal fluorophosphate;
(c) a soluble cyclic alkali metal phosphate;
(d) a soluble linear phosphate; and
(e) a calcium containing substance, selected from the group consisting of calcium citrate and calcium tartrate, and wherein the concentration of components (a)+(b), calculated as F, is 250-500 ppm in a mouth wash, 1000-1500 ppm in a toothpaste, 5000-7500 ppm in a prophylactic paste, and 10,000-15,000 ppm in an application liquid or gel; the concentration of component (c) is 0.1-5% by weight; the concentration of component (e) is 0.05-5% by weight; and the concentration of component (d) is such to provide a Ca:P atomic ratio of about 1.66:1.

2. A dentifrice according to claim 1, wherein said fluoride (a) is sodium fluoride; said fluorophosphate (b) is sodium monofluorophosphate; said cyclic phosphate (c) is sodium trimetaphosphate; said linear phosphate (d) is at least one of phosphoric acid, sodium orthophosphate, sodium tripolyphosphate, sodium tetrapolyphosphate, sodium pyrophosphate, and sodium hexametaphosphate; and said calcium containing substance (e) is at least one of calcium citrate, calcium tartrate, calcium adipate, calcium zeolite, and calcium apofyllite.

3. A dentifrice according to claim 2, wherein said linear phosphate (d) is phosphoric acid, sodium orthophosphte or phosphoric acid plus sodium orthophosphate, and said calcium containing substance (e) is calcium citrate or calcium tartrate.

4. A dentifrice according to claim 1 wherein the ratio of component (a) to component (b), calculated as F, is about 3:1.

5. A dentifrice according to claim 2 wherein the ratio of component (a) to component (b), calculated as F, is about 3:1.

6. A dentifrice according to claim 3 wherein the ratio of component (a) to component (b), calculated as F, is about 3:1.

7. A dentifrice according to claim 1 wherein the ratio of component (a) to component (b), calculated as F, is about 3:1.

8. A dentifrice according to claim 7 which is a mouth wash.

9. A dentifrice according to claim 7 which is a toothpaste.

10. A dentifrice according to claim 7 which is a prophylactic paste.

11. A dentifrice according to claim 7 which is an application liquid or gel.

12. A toothpaste according to claim 1 comprising 0.22% by weight of sodium fluoride, 0.36% by weight of sodium monofluorophosphte, 0.40% by weight of sodium orthophosphate, 0.30% by weight of phosphoric acid, 0.25% by weight of sodium trimetaphosphate, and 0.6% by weight of calcium citrate.

13. A dentifrice according to claim 1 which is a toothpaste having the formulation in parts by weight:

| | |
|---|---|
| Aluminum oxide | 35.0 |
| silicon oxide | 2.0 |
| glycerol | 20.0 |
| carboxymethyl cellulose | 1.5 |
| sodium lauryl sulphate | 2.0 |
| peppermint oil | 1.0 |
| sodium saccharinate | 0.2 |
| sodium fluoride | 0.22 |
| sodium monofluorophosphate | 0.36 |
| primary sodium phosphate | 0.40 |
| phosphoric acid | 0.30 |
| sodium trimetaphosphate | 0.25 |
| calcium citrate | 0.6 |
| Na—methyl p-hydroxybenzoate | 0.10 |
| water to make | 100. |

14. A dentifrice according to claim 1 wherein said fluoride (a) is an alkali metal fluoride.

15. A dentifrice according to claim 14 wherein said alkali metal fluoride is sodium fluoride.

16. A dentifrice according to claim 1 wherein said alkali metal fluorophosphate (b) is sodium fluorophosphate.

17. A dentifrice according to claim 1 wherein said cyclic alkali metal phosphate is sodium trimetaphosphate.

18. A dentifrice according to claim 1 wherein said soluble linear phosphate is selected from the group consisting of phosphoric acid, alkali metal orthophosphates, alkali metal tripolyphosphates, alkali metal tetrapolyphosphates, alkali metal pyrrophosphates, and alkali metal hexametaphosphates.

19. A dentifrice according to claim 18 wherein said soluble linear phosphate is selected from the group consisting of phosphoric acid and sodium orthophosphate.

* * * * *